United States Patent [19]
McCormick

[11] Patent Number: 5,360,423
[45] Date of Patent: Nov. 1, 1994

[54] MEANS FOR SAFE COLLECTION AND TRANSFER OF BODY FLUIDS

[76] Inventor: William McCormick, 65 Hickory La., Carlisle, Mass. 01741

[21] Appl. No.: 66,221

[22] Filed: May 25, 1993

[51] Int. Cl.⁵ ............................................... A61B 19/00
[52] U.S. Cl. ................................... 604/403; 604/192; 604/197; 604/263
[58] Field of Search ................ 128/912, 917, D26; 604/110–111, 161–162, 166–167, 192, 197–199, 240–241, 256–257, 263, 905, 403

[56] References Cited

U.S. PATENT DOCUMENTS

| | | | |
|---|---|---|---|
| 3,468,309 | 9/1969 | Drewe | 604/263 |
| 3,993,063 | 11/1976 | Larrabee | 604/197 |
| 4,232,669 | 11/1980 | Nitshke | 604/192 |
| 4,786,281 | 11/1988 | Valentini et al. | 604/905 |
| 4,943,284 | 7/1990 | Erlich | 604/263 |
| 4,950,260 | 8/1990 | Bonaldo | 604/905 |
| 5,078,694 | 1/1992 | Wallace | 604/192 |
| 5,135,496 | 8/1992 | Vetter et al. | 604/111 |
| 5,247,972 | 9/1993 | Tetreault | 604/905 |
| 5,279,582 | 1/1994 | Davison et al. | 604/263 |
| 5,279,583 | 1/1994 | Shober, Jr. et al. | 604/905 |
| 5,290,254 | 3/1994 | Vaillancourt | 604/192 |

FOREIGN PATENT DOCUMENTS 253426 5/1963 Australia .................. 604/240

*Primary Examiner*—Randall L. Green
*Assistant Examiner*—P. Zuttarelli
*Attorney, Agent, or Firm*—Low and Low

[57] ABSTRACT

A simple and versatile system for the safe transfer and collection of body fluids, such as blood, wherein an enlarged generally cup-shaped guide port receives therewithin the transfer needle which is recessed rearwardly from the open end of the guide port whereby the transfer needle assembly may be manipulated without likelihood of needlestick injury to the health care worker. Larger Guide ports have apertured caps to facilitate and guide a transfer receiver into contact with the needle as well as to isolate further the worker's hand from the contaminated needle. A plurality of sizes of guide ports are provided for varying fluid receivers, with all having common interlocking means for the transfer needle assembly.

19 Claims, 6 Drawing Sheets

MEANS FOR SAFE COLLECTION AND TRANSFER OF BODY FLUIDS

BACKGROUND OF THE INVENTION

In medical diagnostic practice, biological specimens of blood and other bodily fluids are obtained from a patient and subsequently analyzed for the presence of infectious pathogens, biochemical constituents, or the like. Specimen collection and processing routinely involve the handling of used and contaminated medical needles by health care workers. This invention provides a means and method whereby liquid specimen collection and transfer procedures are significantly safer and less hazardous for medical technicians, nurses and the like.

With conventional devices for collection of such specimens, there is a very real danger from accidental needlestick injury associated with transferring the fluid specimen from the patient into the blood specimen collection tube, in which latter the specimen is transported to the laboratory for analysis. Such transfer is commonly effected by manual manipulations of a syringe, a pointed needle cannula, and a receptacle or other sterile receiver having a puncturable rubber stopper.

In one common procedure, a syringe barrel, which is provided with a male connector fitting, is filled with blood. This is often accomplished by connecting the male fitting of the syringe to the female fitting of the access port of a venous access line. The line provides the fluid conduit between the blood vessel and the internal chamber of the syringe barrel. The syringe is filled with blood by withdrawing blood from the blood vessel through the conduit. The blood-filled syringe is then disconnected from the line and an unshielded conventional syringe needle, with a female fitting, is affixed to the syringe barrel. While the medical technician holds the blood specimen collection tube or other specimen receiver in place with one hand, the needle of the blood-filled syringe is used to puncture the rubber stopper or septum of the blood specimen collection tube. The process of puncturing the collection vessel stopper is accomplished by the technician holding the syringe with the other hand and aiming the blood-filled syringe/needle assembly to the appropriate stopper penetration spot.

The above described practice of holding a collection tube in one hand and moving the blood-filled syringe/needle assembly toward the tube stopper with the other hand constitutes a grave danger for the medical technician. If for example, the technician misses the tube stopper and punctures instead the hand holding the collection tube, the technician could contract an infection from any pathogens, such as the AIDS virus or a hepatitis virus present in the blood specimen.

Of further significance, blood specimen collection tubes or bottles used commonly for diagnostic procedures have a variety of access port diameter sizes. The access port is the rubber stopper or septum which serves as the closure of the container which is punctured by the needle of the transfer device needle, such as the type commonly affixed to a syringe barrel. As presently practiced, needles used for the syringe in specimen transfer procedures are not shielded and are commonly implicated in needlestick injuries of health care givers.

In standard blood collection devices, multiple sample adapters are provided at the sample collection end of indwelling catheters or winged needle sets. The multiple sample adapter is a needle which is assembled with a flexible rubber sleeve which reversibly covers the needle as it penetrates and is withdrawn from rubber stoppers of liquid specimen collection vessels. The purpose of the sleeve is to interrupt blood flow after the needle is withdrawn from the tube stopper. Flow is reinitiated after the sleeve is pushed back as the needle penetrates another stopper.

Although the sleeve is helpful in stopping blood flow from the source of the blood for sample collection, it does not prevent the health care worker from sustaining an accidental needle stick injury. Thus, some multiple sample adaptor devices are designed to be reversibly assembled with needle shields in which the needle is recessed within a long tubular or short bell-shaped guide which fits over the blood specimen collection ports. The needle is recessed within the tube guide, and this configuration partially blocks the direct exposure of the hands of the technician to the contaminated needle.

The deficiencies of the current devices are that a multitude of combinations of tubular guides or bell-shaped guides require the technician to assemble and disassemble various multiple sample needles with guides of different sizes to accommodate the variety of specimen tube stopper port and specimen containers used commonly for either blood chemistry or for determination of the presence of blood-borne pathogens. For example, blood chemistry tubes have narrow-diameter rubber stopper ports; whereas, many blood culture specimen bottles, used for growing infectious pathogens to diagnose infections, have relatively wide septum ports. Thus, a narrow tube guide for chemistry tubes will not fit over wide port septums.

Of further significance is that conventional syringe needles have no multiple sample features and no provisions for tube guides or large guides for shielding the needles during fluid specimen transfer procedures from syringe barrel to liquid specimen container.

BRIEF SUMMARY OF THE INVENTION

The present invention markedly improves upon the blood handling and transfer techniques as presently practiced. In so doing, uniquely simple and effective devices are provided in accordance with the invention.

The objects of this invention are achieved as set forth herein and include as features:

To provide a fully assembled means with a female connection for safe transfer of blood specimen or other fluid specimen from a syringe barrel to a specimen collector, whereby the multiple sample needle of said means, which punctures the stopper or septum of the collection vessel, is recessed within a shield, which greatly reduces the risk of accidental needlestick but allows facile access to the puncture of the tube, thereby establishing a fluid-flow path from the chamber of the syringe barrel to the chamber of the collection tube. Further the invention provides a specimen collection guide with a large diameter port, and with a cap which is detachably affixed over the large open end of the guide and allows for subsequent safe specimen transfer to narrower tube stoppers. The cap means serves to protect further against exposure to needlestick injury and also to enclose the multiple sample needle for subsequent disposal.

To provide a cap means to affix interengagably to and to cover further the shielded multiple sample needle in the case of use of transfer sequentially first to specimen collection vessels with wide diameter orifice covers and then to blood collection tubes with small diameter orifice covers, whereby said cap provides a locking engagement mechanism which allows facile overall affixation of the bell on the cap and a repeated sequential access of smaller tubes to multiple sample needles, and which cap provides a substantially smaller central opening for smaller diamter collection tubes, the cap having a flange or outwardly directed edge around the smaller opening, thereby to discourage or minimize likelihood of a user's finger to inadvertently go through the smaller hole and thereby be exposed to a hazardous needle.

To provide a series of port guides of various sizes and shapes, each of which may be irreversibly and non-rotatably affixed to either a female or a male multiple sample needle assembly which multiple sample assemblies have identical means for the irreversible, non-rotatable affixment to any of the port guides of the collection.

To provide a safe method to transfer of a liquid from a syringe to a specimen collection tube with an appropriately sized port guide having been assembled irreversibly with a multiple sample needle with female connection means for affixment to conventional syringes.

To provide a safe method to transfer sequential portions of a liquid from a syringe to a series of first large diameter port specimen collection vessels, such as blood culture bottles, and next smaller diameter port blood collection tubes, using a single large port guide with female connection multiple sample needle for syringe attachment and with a safety cap which is snapped in place on the open end of the port guide.

To provide a safe method to collect a sample from an indwelling venous access line sequential portions of blood directly into a series of first large diameter port specimen collection vessels, such as blood culture bottles, and next small diameter port blood collection tubes, using a single large port guide with male connector multiple sample needle for attachment to said line and with a safety cap which is snapped in place on the open end of the port guide.

BRIEF DESCRIPTION OF THE DRAWINGS

This invention will be better understood when taken with the accompanying drawings, in which.

DESCRIPTION OF THE PREFERRED EMBODIMENTS

Figure 1:
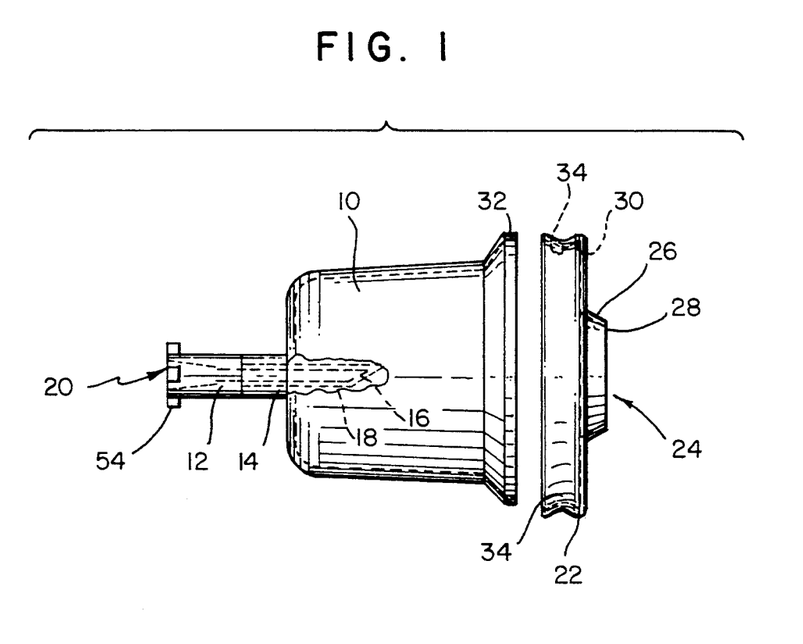
FIG. 1 is an exploded side view of one embodiment of the invention showing a large sample port guide with a recessed multiple sample needle, and a safety cap with a small port access hole.
Figure 2:
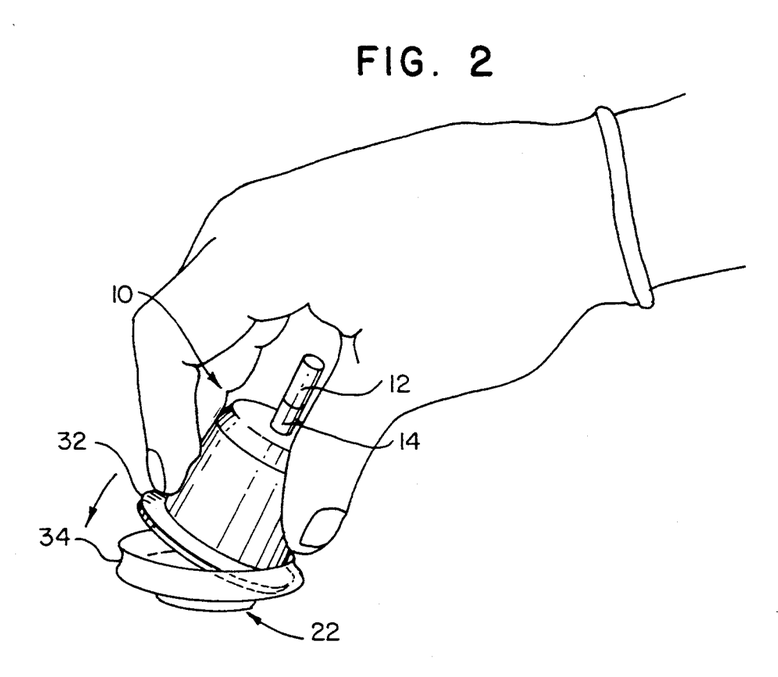
FIG. 2 illustrates the one-handed manner for affixing the port guide to the safety cap.

Referring to the drawings, FIGS. 1–4 show preferred embodiments of the invention incorporating the unique features and basic concepts thereof. Thus, FIG. 1 shows a large port sampling shield guide 10 assembled irreversibly with a needle subassembly 12. Guide 10 includes a connector extension 14 at its proximal end receiving a multiple sample needle device 12 including a needle 16, over which a penetrable, flexible sleeve 18 is disposed and which subassembly 12 is provided at its proximal end with a female connector 20. The separate safety cap 22 associated with guide 10 is a lid-type element having a smaller central hole 24 therethrough, said hole being defined by an outwardly projecting tapered circular protrusion 26 terminating in edge 28. Safety cap 22 can be detachably affixed to shield 10 by an interference snap fit, wherein internal circular groove 30 of cap 22 engages outwardly flared circular lip 32 as internal bead 34 of cap 22 is forced thereover in a one-handed procedure depicted in FIG. 2. While cap 22 is shown as a detached element, it is within the scope of the invention to hinge, tether, or otherwise secrure the cap to the guide 10.

Figure 3:
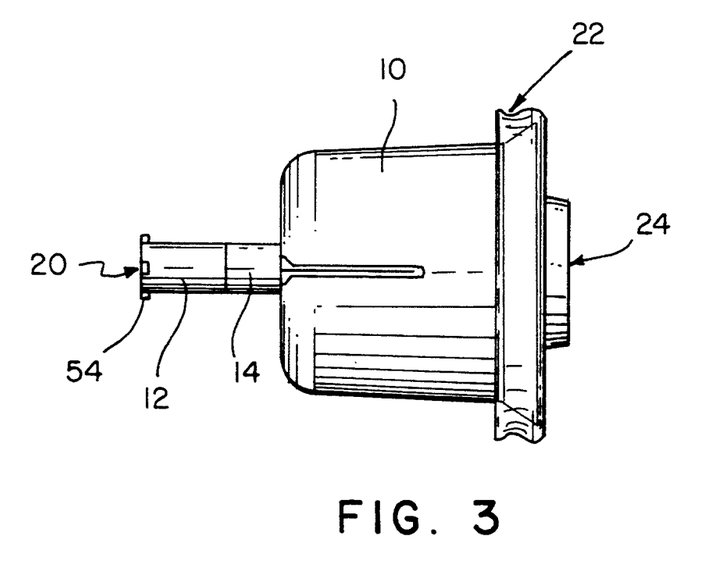
FIG. 3 is similar to FIG. 1 wherein a large port sample guide has the safety cap affixed by a flexible snap fit and having a female connector.
Figure 4:
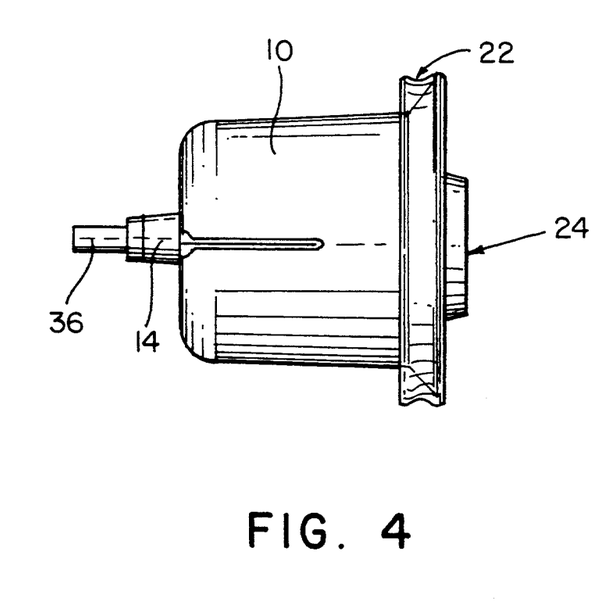
FIG. 4 is similar to FIG. 3 but having a male connector.

FIG. 3 shows safety cap 22 affixed to shield guide 10, which guide is assembled with the needle subassembly 12 having the female connector end 20. FIG. 4 is similar, but depicts an alternative form of the invention in which safety cap 22 is similarly snap-affixed to shield guide 10, which shield guide is assembled irreversibly with subassembly 12 having a male proximal connector 36 instead of the female connector 20.

The device shown in FIG. 3, is used for the safe transfer of a liquid specimen from a syringe barrel to a large port blood collection vessel such as is used for blood culture procedures, as set forth hereinafter. The similar device of FIG. 4 (except having the male connector) is used for direct collection as from a venous indwelling line directly to a large port blood culture collection vessel. In either form of the invention of FIGS. 3 and 4 the reversible attachment of safety cap 22 with large port sample guide 10 is accomplished by pressing guide 10 and cap 22 together as in FIG. 2.

The external configuration of cap 2, particularly with the outwardly projecting circular edge 28 surrounding and defining hole 24, is a basic aspect of this invention. The tapered circular flange 26 and edge 28 serve to discourage the inadvertent contact of a finger of the human hand with a contaminated needle 16 disposed within the guide assembly 10. The outwardly directed edge 28 is designed to engage and deflect the health care worker's fingers, and preclude the fingers from sliding therepast into the guide and in the direction of needle 16. Safety cap 22 also serves to enhance the safe disposal of the guide/multiple sample needle device. The cap 22 is left in place on guide 10 after the medical procedure is complete. Cap 22 thus serves generally to enclose the contaminated needle 16 within guide 10 during waste disposal-related handling.

The specific means for irreversibly assembling either a male or female multiple sample assembly 12 with any of a variety of large and small port guides 10 of this invention is shown in FIGS. 5-9. Thus, a port guide 10 of any size, is provided with a common means whereby the guide 10 is irreversibly assembled with a sample assembly 12 having either a female proximal connector 20 or a male connector 36. Thus, tubular connector 14 is formed and extends from the proximal end of guide 10 with a configured bore extending from proximal end 38 to internal distal opening 40. The internal surface of the bore adjacent proximal end 38 contains a series of longitudinal indentations 42 extending a short distance along the longitudinal axis of tubular connector 14. The bore abruptly increases in internal diameter at 44 near distal end 40.

The combination of the bore of extension 14, the indentations 42 and the abrupt edge at 44 are common to all port guides of this invention and is complementary to the outside configuration of the assembly engagement means of either the male or female multiple sample needle subassemblies.

Subassemblies 12 as seen in FIGS. 5-9 are comprised of three components: needle 16, gripper base 46, and flexible, retractable needle sleeve 18. In a preferred embodiment, needle 16 is a stainless steel hollow cannula having a pointed end 48 and a flat base end 50. Gripper base 46 may be a hard thermoplastic such as polyvinyl chloride formed by conventional molding processes.

Figure 5:
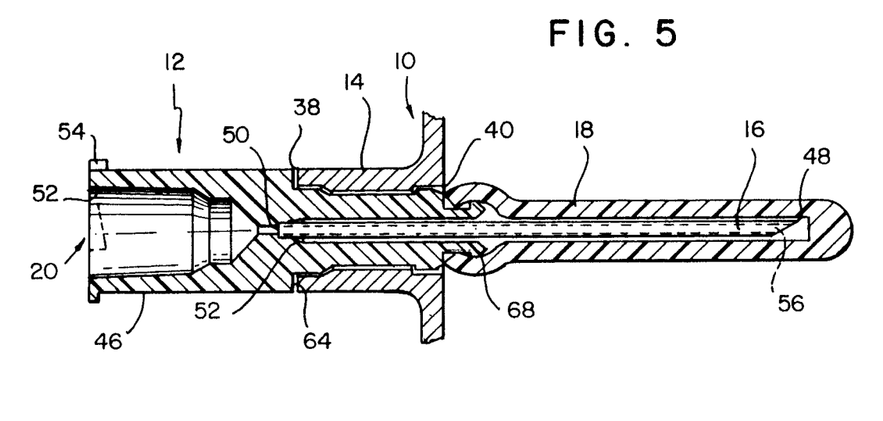
FIG. 5 is an enlarged cross-sectional view of the shield guide of FIG. 1 irreversibly assembled with a multiple sample needle assembly.

In FIG. 5, female subassembly 12 is provided with a conventional tapered opening 52, for assembly with a conventional male syringe connection. Cam-locking projections 54 may be optionally provided. The base 46 is generally cylindrical in shape with a bore of varying diameter therethrough. Needle 16 has a uniform external cylindrical surface and a hollow bore 56 therethrough, and is assembled with base 46 by fitting the proximal end of needle 16 into the distal opening portion of member 46 which is designed to accept a defined length of the proximal end of needle 16. This length is determined by the proximal end of needle 16 abutting inwardly extending ridge 58 which is disposed circumferentially within the bore of base 40. Needle cannula 16 is assembled irreversibly with base segment 40 by a combination of mechanical interference fit between the external surface of the proximal segment of needle cannula 16 and the internal cylindrical profile 60 of the distal opening of 12. This assembly can further be enhanced by the use of a conventional adhesive agent to bond the needle 16 to the internal bore surface 60 of base 46.

Figure 6:
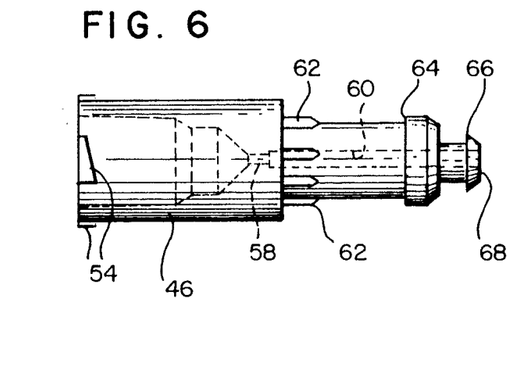
FIG. 6 is a side elevation of the needle assembly female connector of FIG. 3.
Figure 7:
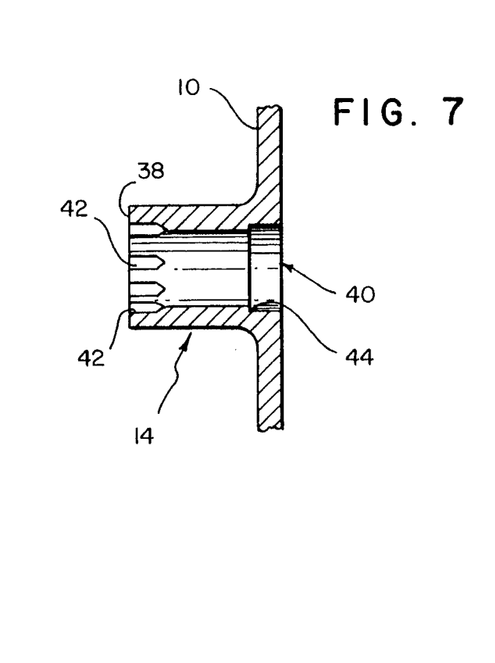
FIG. 7 is a sectional view of the guideport connector extension of FIG. 3.
Figure 8:
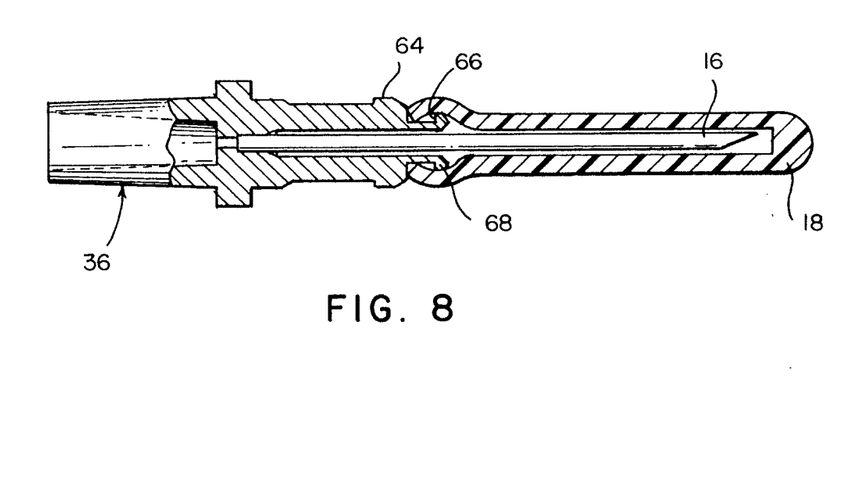
FIG. 8 shows a multiple sample needle subassembly similar to FIG. 5, but having a male connection at its proximal end.

Base section 46 is shown in FIG. 6 to illustrate the external surface profile thereof. The external surface of base section 46 is provided toward its distal end with a series of longitudinally disposed projections 62 and circumferentially disposed spaced ribs 64 and 66. A radial abutting surface 68 is provided proximally adjacent to rib 64. The external profile of the female connector subassembly and the male subassembly (FIGS. 4 and 9) are identical with respect to elements 62, 64 and 66.

The irreversible assembly of system 12 or with connector 14 of port guide 10, is accomplished by force fitting distal end 68 of the subassembly through the proximal end 36 of the guide extension segment 14. This snap fit is completed when annular surface 64 of the subassembly abuts the proximal annular surface 44 of the port guide 14 to lock the members together. Interference between projections 62 of subassembly 12 with indentations 42 of guide 14 prevents rotation around the longitudinal axis of the assembly. The complete assembly is shown in cross-section in FIG. 5. This figure also shows flexible sleeve 18 slipped over needle 16. Sleeve 18 is affixed over the distal end of needle 16 and is held thereon by being slipped over and engaging the circumferentially disposed edge 64 located adjacent to rib 66. Otherwise, the element 31 is identical to the corresponding aspects of female subassembly 12.

Figure 9A:
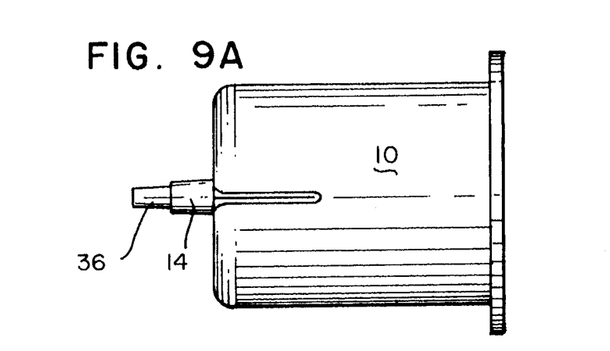
FIGS. 9A–9F show three varying-size port guides to which either male or female distal end multiple sample needle subassemblies are irreversibly assembled.
Figure 9B:
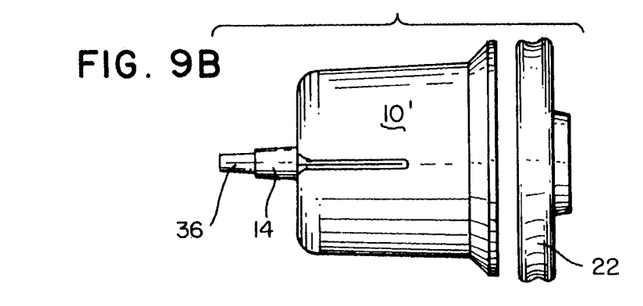
Figure 9C:
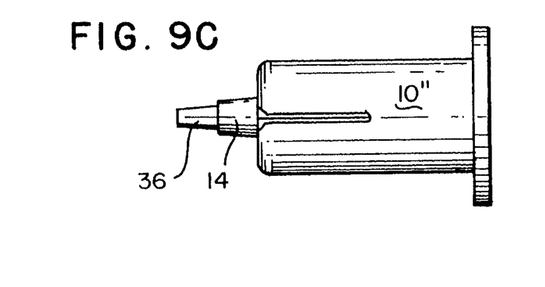
Figure 9D:
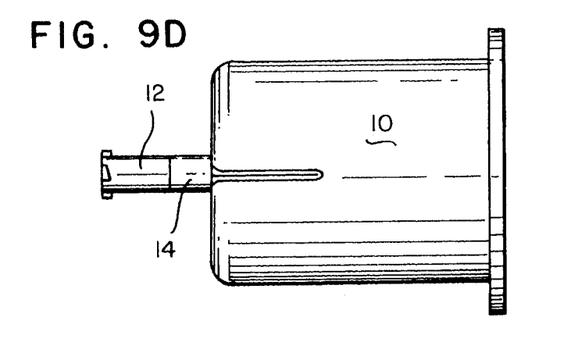
Figures 9E, 9F:
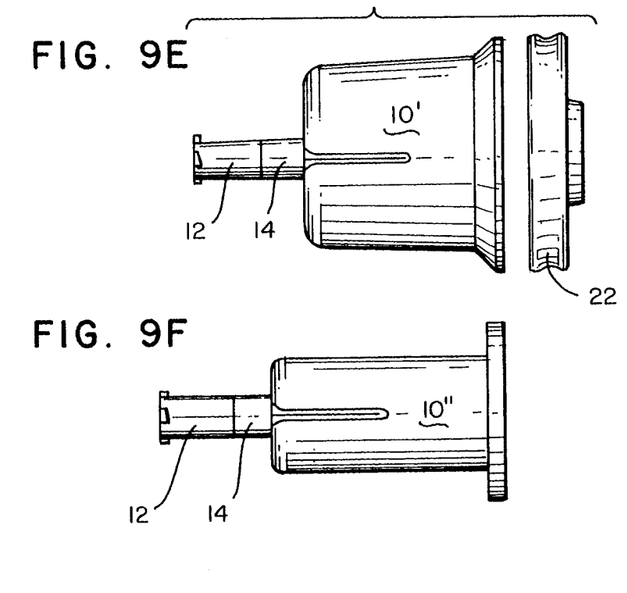

FIGS. 9A-9F illustrate an aspect of this invention in which a variety of different-sized port guides are provided which can be used for a multiplicity of large and small diameter ports for diverse specimen collection vessels and tubes. The guides 10', 10, and 10" of FIGS. 9A, 9B and 9C are provided with male subassemblies 36 for connection to the usual female connector ports of indwelling venous access lines. Thus, these safety devices can be used to collect blood specimens directly from the patient's blood vessel into blood specimen collection vessels, the internal chambers of which are accessed by entry of needle 16 into the vessels. The similar devices of FIGS. 9D, 9E and 9F are provided with female connector ends 12 and are therefore useful for the safe transfer of liquid specimens from conventional syringes to collection vessels of various port diameters, the interiors of which containers can be accessed by a needle-puncturable port through which needle 16 is placed during specimen transfer.

The commonality and simplicity of the means for assembly of the various combinations of subassembly to the port guide comprises a further aspect of this invention which facilitates the economic manufacture of a variety of liquid transfer and collection device, and wherein the port guide as at 10 provides unique facile safe manipulation.

The devices of the invention provide the basis for new procedures for the direct collection of blood from the patient into specimen containers, as well as new methods for the safe transfer of liquid specimens from conventional syringes. These novel procedures constitute another aspect of the present invention and are described hereinbelow.

Figure 10A:
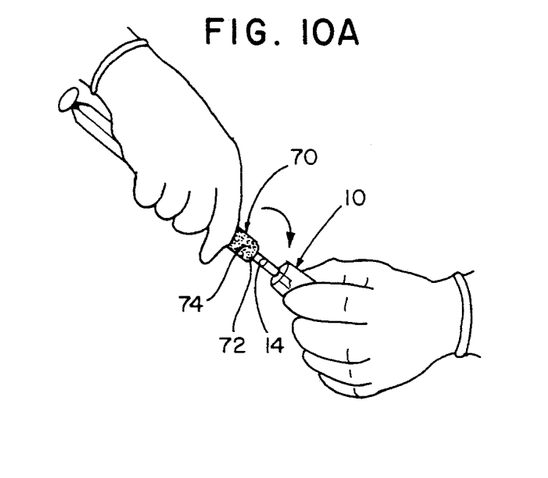
FIGS. 10A–10D are a sequence of illustrations depicting one method of the invention comprising the safe transfer of liquid specimens from a syringe to either a standard blood collection tube or a standard blood culture tube with a tube port guide irreversibly assembled with a female multiple sample needle subassembly.
Figure 10B:
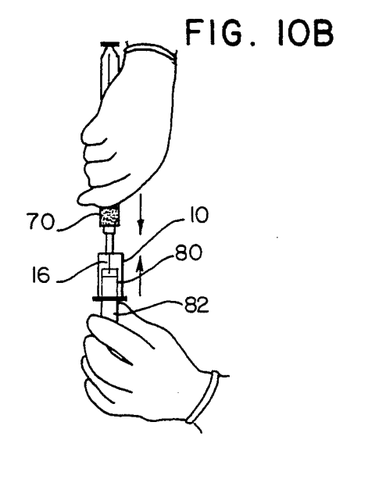
Figure 10C:
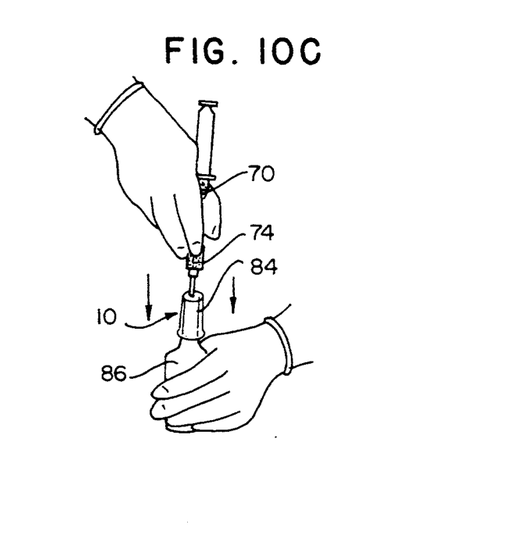
Figure 10D:
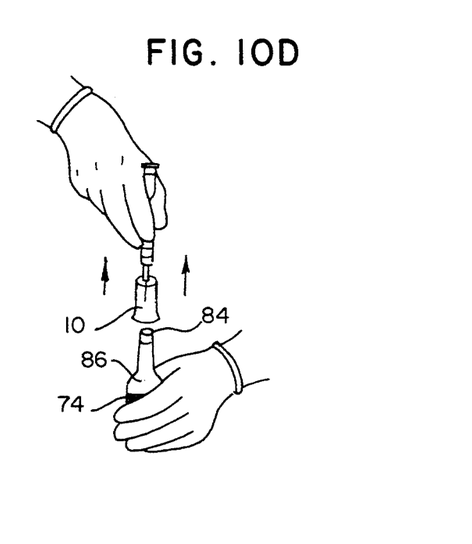

One method in accordance with this invention is depicted in FIGS. 10A-10D in which a liquid specimen is safely transferred from a syringe to a blood sample tube. This method includes the following sequential steps:

As shown in FIG. 10A, a conventional syringe 70 having a male connector 72 and containing a liquid biological specimen 74, is affixed to the female connector 12 of a blood sample tube port guide assembly 10 of the type and size shown in FIG. 9F, for example. The interengaged syringe and port guide assembly is placed over and shields stopper 80 of blood specimen tube 82 as shown in FIG. 10B or the port 84 of a blood culture tube 86 as shown in FIG. 10C. Pressure causes needle 16 to puncture the stopper 80 or 84 causing sleeve 18 to slide back from the needle, and liquid 74 from the syringe 70 barrel can then flow into tube 82 or 86. After the desired amount of specimen 74 is transferred from the syringe to the tube, the syringe is disengaged from the sample tube, as in FIG. 10D, and discarded in its entirety on disassembly, with contaminated needle 12 safely recessed within the tube guide 10 of the transfer assembly.

Figure 11A:
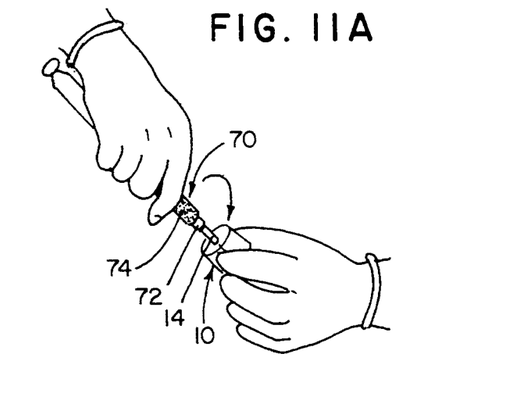
FIGS. 11A–11F are a sequence of illustrations depicting another method of the invention comprising the safe transfer of first portions of a liquid specimen from a syringe first to a large port blood sample vessel and then transferring remaining portions of the liquid specimen of the syringe to one or more small port collection tubes with a large port guide irreversibly assembled with a female multiple sample needle subassembly and reversibly affixed to a port guide safety cap.
Figure 11B:
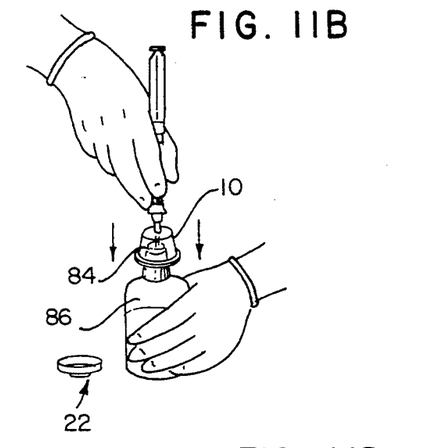
Figure 11C:
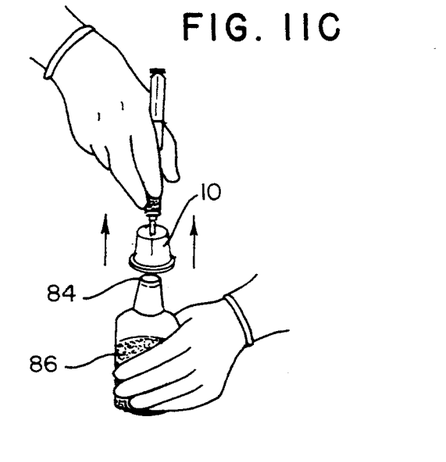
Figure 11D:
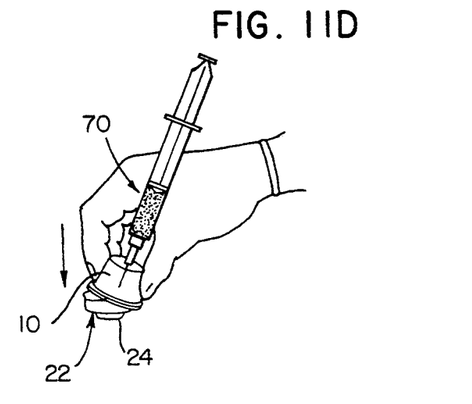
Figure 11E:
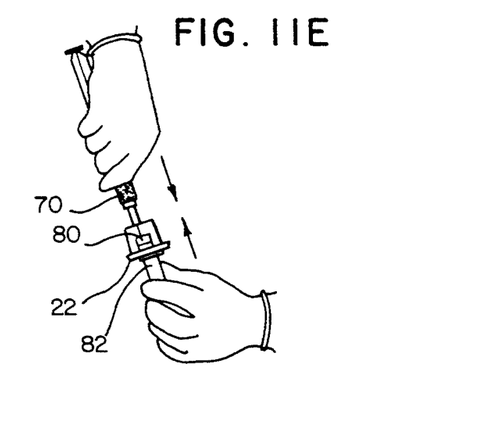
Figure 11F:
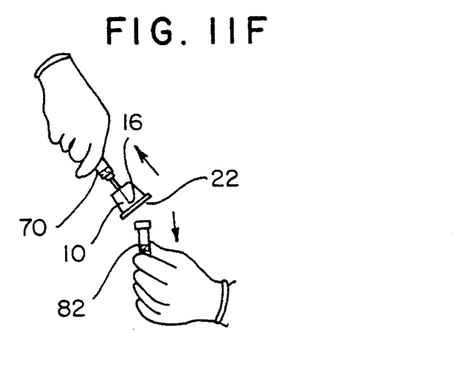

A further method according to this invention is shown in FIGS. 11A–11F. Large-diameter port guide 10 with cap 22 assembled therewith as shown in FIG. 11D, is shown in FIG. 11A with a female connector fitting 14. Guide 10 is affixed to a conventional syringe 70 having a male connector 72 and containing a liquid biological specimen 74. Cap 22 is then removed from guide 10 and set aside for later use. The interengaged syringe and guide assembly is pressed over blood culture bottle 86 as shown in FIG. 11B. Needle 16 punctures stopper 84 causing sleeve 18 to slide back from the needle, and liquid 74 from the syringe barrel 70 can then flow into blood culture bottle 86. After the desired amount of specimen 74 is transferred from syringe 70 to the blood culture bottle, the syringe and port guide are disengaged from the bottle as shown in FIG. 11C and then guide 10 is reattached with cap 22 as shown in FIG. 11D. Subsequently, blood collection tube 82 is positioned through access hole 24 of cap 22 thereby allowing the interengaged syringe and port guide assembly 10 with cap 22 to be pressed over the tube stopper of blood specimen tube 82 as shown in FIG. 11E. Needle 16 punctures the stopper causing sleeve 18 to slide back and liquid 74 from the syringe barrel then to flow into tube 82. After the desired amount of specimen 74 is transferred from syringe 70 to tube 82, the syringe 70/large port guide 10 with cap 22 attached to guide 10 is disengaged from the stopper of the sample tube as shown in FIG. 11F and discarded in its entirety, with the contaminated needle 16 safely recessed within the large port guide 10 and further blocked from accidental exposure by the cap 22 affixed to the guide 10.

Other variations on the method depicted in FIG. 11 will be readily apparent to those in the art. For example, the use of guide 10 and cap 22, and with guide 10 having a male fitting as in FIG. 3, could be applied to the direct collection of blood from an indwelling venous access line, which line has a female connector fitting. Thus a sequence of blood specimens could be collected first into a large port blood collection bottle and then, after attaching cap 22 having access hole 24, then transferred into small stopper port blood collection tubes.

Other related versions of the fundamental teachings of new means and methods of this invention will become apparent to those skilled in the art and such are incorporated as further aspects hereof.

What I claim is:

1. A safe collection and transfer system for body fluids comprising,
    a cup-like tubular guide port of relatively large diameter having a substantially full-diameter open distal end and having a proximal end wall having a smaller diameter opening therein, and a tubular extension extending proximally therefrom for receiving a fluid transfer needle assembly,
    a removable cap for said guide port distal end having a large peripheral diameter,
    said cap having a smaller diameter central opening therethrough than said guide port and said peripheral diameter for receiving and guiding a transfer receiver therethrough and into said guide port when in use,
    said cap and the periphery of said guide port distal end having cooperating elements for detachably securing said cap to said guide port,
    whereby when said system is in use, a needle assembly is received in said guide port extension with the needle positioned fully within the guide port, fluids may be received into the needle assembly adjacent its proximal end from a syringe-like source and delivered therefrom into a puncturable transfer receiver extending through said cap opening and positioned within said guide port open distal end, thereby protecting a health care worker from exposure to the contaminated transfer needle.

2. The collection and transfer system of claim 1 wherein said cap is provided with an externally extending tapered annular flange about said cap central opening, thereby to further preclude approach and contact of the health care provider with the needle.

3. The collection and transfer system of claim 1 wherein said cap is provided with an externally extending annular flange about said cap central opening, thereby to further preclude approach and contact of the health care provider with the needle.

4. The collection and transfer system of claim 1 wherein said guide port includes a rigid outwardly extending annular flange about said distal opening.

5. The collection and transfer system of claim 4 wherein said cap is in cooperative interlocking association with said guide port annular flange to detachably secure said cap to said guide port.

6. The collection and transfer system of claim 1 wherein said port tubular extension includes internal bore configurations for cooperative interlocking association with said needle assembly.

7. The collection and transfer system of claim 6 further including a plurality of said guide ports each of differing diameter at its respective distal end for desired selection for use,
    each of said guide port tubular proximal extensions having substantially identical internal bore configurations, whereby and said needle assembly may be interchangeably connected with any one said differing diameter guide port.

8. The collection and transfer system of claim 7 further including a plurality of caps for use with a selected said guide port distal end.

9. The collection and transfer system of claim 1 further including a said needle assembly cooperatively associated therewith, said needle assembly having:
    a base gripper member including:
        external surface configurations at the distal end thereof for cooperative interlocking association with said port tubular bore configurations,
        a bore therethrough, and,
        a needle fixed in said bore and extending from the distal end thereof,
    whereby when said needle assembly is associated with said guide port, said needle distal end lies within said guide port and spaced from the fully-open distal end thereof, thereby minimizing likelihood of hazardous contact with a health care worker.

10. The collection and transfer system of claim 9 wherein said needle assembly gripper member proximal end includes a male configuration for cooperative fluid transfer association with a conventional indwelling fitting thereby permitting a fluid specimen to be transferred through said guide port.

11. The collection and transfer system of claim 9 wherein the proximal end of said needle assembly gripper member includes a female configuration for cooperative fluid transfer association with a conventional fitting on a syringe having a fluid specimen to be transferred through said guide port.

12. The collection and transfer system of claim 11 wherein said needle prior to engagement with a receiver is enclosed and sheathed within a resilient flexible sleeve to maintain cleanliness and preclude accidental injury.

13. The collection and transfer system of claim 12 wherein the proximal end of said sleeve is detachably connected to the distal end of said gripper member.

14. A method for safe collection and transfer of body fluids comprising the steps of,
providing a cup-like tubular guide port of relatively large diameter having a substantially full-diameter open distal end and a smaller diameter open proximal end, and a tubular extension extending therefrom,
providing a cap having a large peripheral diameter and a smaller diameter central opening for the fully-open guide port distal end,
fitting a fluid transfer needle assembly having a distally extending needle within said tubular extension with the needle extending into said large diameter guide port and terminating short of the full-diameter open end thereof, and,
detachably fitting the cap with the guide port,
whereby a puncturable receiver may be inserted within said cup-like guide port through said cap central opening and engaged with the needle therein, and a supply source of body fluids may be cooperatively associated with said needle assembly at the proximal end thereof, thereby to transfer the body fluids from the source to the receiver without exposure of the needle to the health care worker.

15. The collection and transfer method of claim 14 including the further step of inserting and guiding a puncturable receiver through the apertured cap and into the guide port adjacent the needle, whereby fluid may be transferred through the needle and into the receiver within the guide port and thereby remote from the hand of the health care worker.

16. The collection and transfer method of claim 14 including the step of selecting a fluid transfer needle assembly having a proximal female connector means for association with a conventional fluid syringe male distal end.

17. The collection and transfer method of claim 14 including the step of selecting a fluid transfer needle assembly having a proximal male connector means for association with a conventional indwelling fitting having a female distal end.

18. A method for safe collection and transfer of body fluids, comprising the steps of,
providing a cup-like tubular guide port of relatively large diameter having a substantially full-diameter open distal end and a smaller diameter open proximal end, and a tubular extension extending therefrom,
providing a cap having a large peripheral diameter and a smaller diameter central opening for the fully-open guide port distal end,
fitting a fluid transfer needle assembly having a distally extending needle within said tubular extension with the needle extending into said large diameter guide port and terminating short of the full-diameter open end thereof,
placing the guide port over and around the neck of a blood culture container and concurrently inserting the said needle into the container,
withdrawing a specimen of the blood culture from the container,
removing the guide port and needle from the container, and,
detachably fitting the cap with the guide port,
whereby after a receiver is inserted within said cup-like guide port through said cap central opening and engaged with the needle therein, and a supply source of body fluids is cooperatively fluidly associated with said needle assembly at the proximal end thereof, the body fluids may be transferred from the source to the receiver without exposure of the needle to the health care worker.

19. The method for safe collection and transfer of body fluids of claim 18 including the further step of inserting and guiding a puncturable receiver through the apertured cap and into the guide port adjacent the needle, whereby fluid extracted from the container may be transferred through the needle and into the receiver within the guide port and thereby remote from the hand of the health care worker.

* * * * *